United States Patent [19]

Benoist

[11] Patent Number: 5,779,703
[45] Date of Patent: Jul. 14, 1998

[54] DEVICE AND METHOD FOR POSITIONING AND HOLDING BONE FRAGMENTS IN PLACE

[76] Inventor: Louis Armand Benoist, 1700 Skeels Ave., Eau Claire, Wis. 54701

[21] Appl. No.: 749,006

[22] Filed: Nov. 14, 1996

Related U.S. Application Data

[60] Division of Ser. No. 403,628, Mar. 14, 1995, Pat. No. 5,591,169, which is a continuation-in-part of Ser. No. 260,412, Jun. 14, 1994, abandoned.

[51] Int. Cl.[6] ................................................. A61B 17/56
[52] U.S. Cl. .......................... 606/54; 606/59; 606/69
[58] Field of Search ................................. 606/54, 55, 56, 606/57, 59, 69, 70, 71

[56] References Cited

U.S. PATENT DOCUMENTS 4,127,119  11/1978  Kronner ..................................... 606/59

*Primary Examiner*—Michael Buiz
*Assistant Examiner*—Julian W. Woo
*Attorney, Agent, or Firm*—Breiner & Breiner

[57] ABSTRACT

A bone organizer or template for positioning K-wires or the like in bone fragments and holding the K-wires in place while the fracture mends is described. The invention also provides a simplified method of reducing a distal radius fracture by placing a plurality of K-wires into the bone fragments of the fracture in a plurality of planes, and after the K-wires are inserted into the bone fragments, they are inserted into a bone organizer and anchored in place to the bone organizer to hold the bone fragments together while mending.

6 Claims, 4 Drawing Sheets

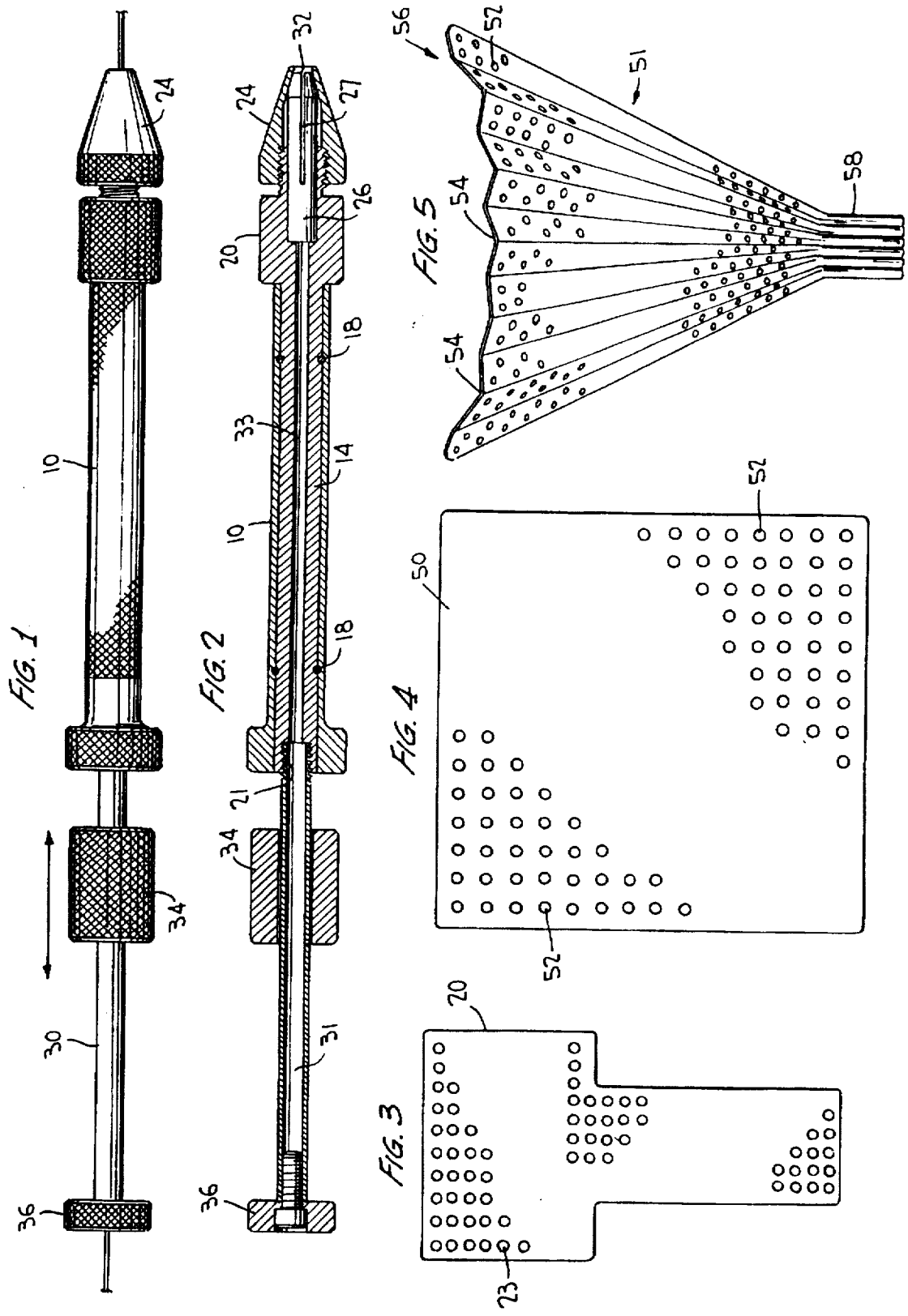

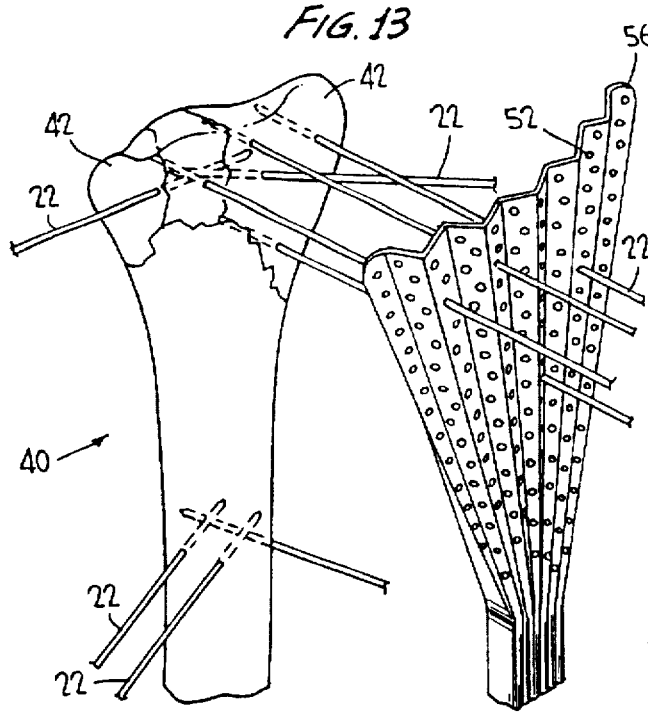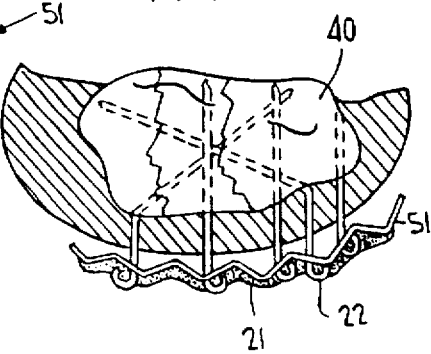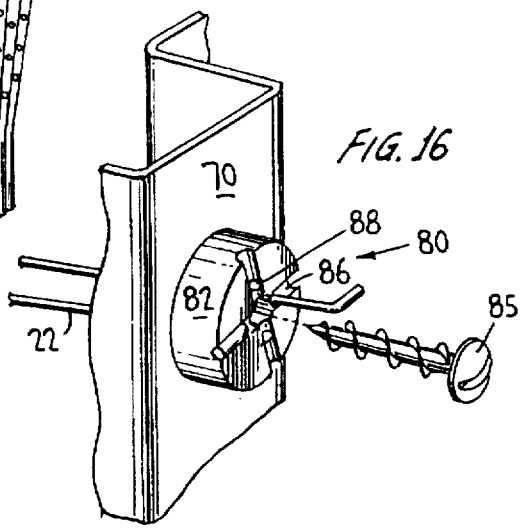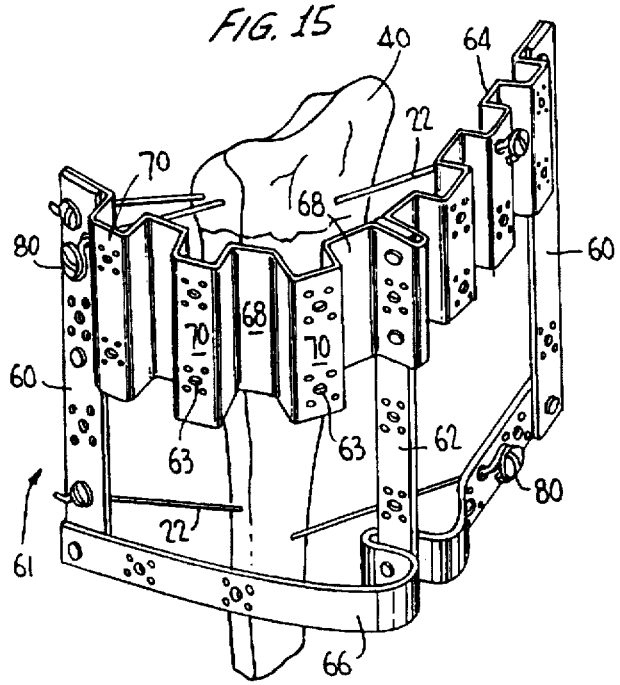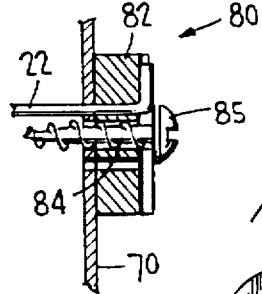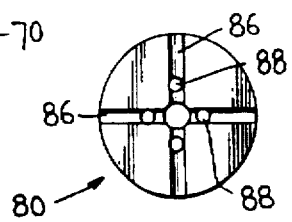

5,779,703

DEVICE AND METHOD FOR POSITIONING AND HOLDING BONE FRAGMENTS IN PLACE

RELATED APPLICATIONS

This is a division of application Ser. No. 08/403,628 filed Mar. 14, 1995, now U.S. Pat. No. 5,591,169, which in turn is a continuation-in-part of application Ser. No. 08/260,412 filed Jun. 14, 1994, now abandoned.

FIELD OF INVENTION

This invention relates to a bone organizer or template for positioning K-wires or the like in bone fragments and holding the K-wires in place while the fracture mends, and to a method of positioning and holding bone fragments. More particularly, the invention relates to a bone fragment organizer or template which is of simple construction, is relatively inexpensive, and can be used with K-wires to maintain the K-wires in place while a fracture mends. This is an external fixator.

BACKGROUND OF INVENTION

Devices are known for use by surgeons to position bone fragments in place or to reduce a fracture, which are essential in organizing bone fragments. Devices are shown for example in U.S. Pat. Nos. 5,254,119; 5,250,048; 5,100,408; 4,901,711; 4,703,751; 4,421,112; and 4,037,592. Moreover, U.S. Pat. No. 4,414,967 discloses staple means for tying bone fragments together to permit the bone to mend properly. See also U.S. Pat. Nos. 2,301,500 and 5,139,498.

It is also recognized in the art that particular problems are associated with fractures of the wrist commonly referred to as distal radius fractures. One publication describing the reduction and treatment of distal radius fractures is *Hand Clinics: External Fixation*, Editor Richard A. Berger, Volume 9, Number 4, November, 1993, at page 587 and following. The latter publication describes various devices and means of repairing and fixation of distal radius fractures. In this publication, the use of K-wires for holding bone fragments in place is also described. All of the devices disclosed, however, are complex in nature and accordingly are expensive. There is a need, therefore, for a simple device and method for repairing bone fractures, particularly fractures of the wrist.

OBJECTIVES AND SUMMARY OF INVENTION

Accordingly, it is a primary object of the present invention to provide a simple device for use in the reduction and fixation of distal radius fractures and to provide a method of fixating a distal radius fracture and holding the fractured bone in place while mending.

It is another object of the present invention to provide a simplified template which can be adjusted depending upon the size of the wrist bone and which can be used with simple fractures as well as fractures where the bone has been reduced to a number of pieces.

The aforesaid and other objects of this invention are accomplished by providing a template or bone organizer comprised of a light weight metal sheet, such as an aluminum sheet, having a plurality of holes. Most preferably the device will have an arcuate shape produced by taking a square piece of thin metal sheeting having a plurality of randomly placed holes and forming it into a series of corrugations. "Randomly placed holes" as used herein means that the location of the holes on the template is not critical—they can be in a pattern or not in a pattern. This device can be used to receive a plurality of K-wires positioned in the bone fracture in a number of different planes by adjusting and shaping the corrugated portion of the device to receive and accommodate the K-wires. Once the K-wires are inserted into the holes of the template or the bone organizer, the ends of the wires are held firmly in place using a specially constructed grommet or fastener. Less preferably a common adhesive cement, such as a-polymer adhesive cement, can be used. The template and K-wires are left in place while the fracture mends and thereafter removed and discarded. The grommet or fastener is preferred over cement in that the K-wires can be more easily removed if there is difficulty in mending of the fracture or the like.

Accordingly, the present invention provides a simple but effective bone organizer and method of reduction and fixation of a fracture, particularly a fracture of the wrist. Unlike many of the prior art devices, it is not necessary to have the device extend across the wrist to the hand, providing for greater freedom of movement to the patient wearing the device.

THE DRAWING AND DETAILED DESCRIPTION

In the drawing,

FIGS. 1 and 2 illustrate a preferred surgical hammer for positioning K-wires within a fracture;

FIG. 3 illustrates a first embodiment of a bone organizer or template;

FIG. 4 illustrates a sheet of material intermediary in forming a preferred bone organizer or template shown in FIG. 5;

FIG. 5 illustrates one preferred template or bone organizer fabric a ted from the sheet shown in FIG. 4;

Figure 10:
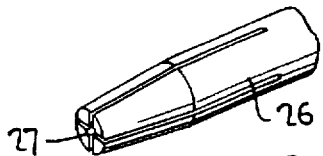
Figure 11:
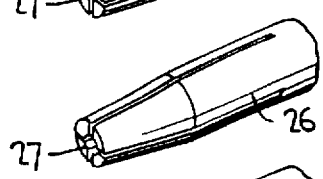
Figure 12:
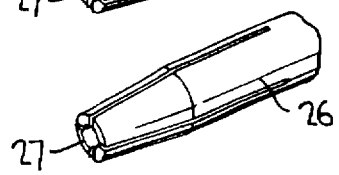
Figure 19:
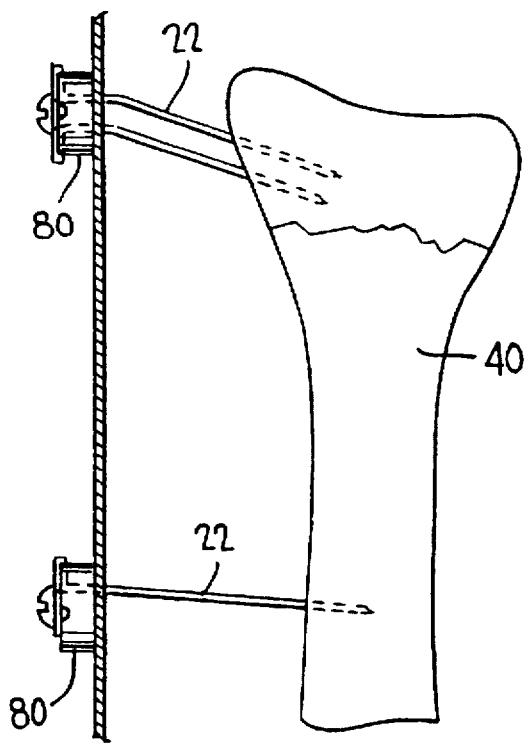
Figure 20:
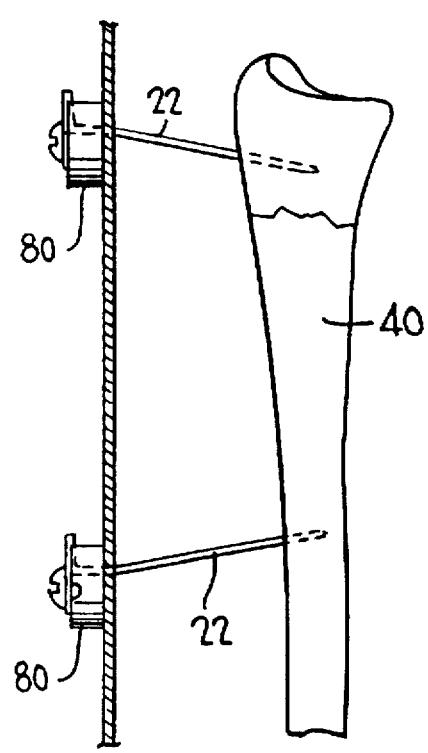

FIGS. 10, 11, and 12 illustrate collets for receiving wires of varying diameter for use in the surgical device of FIGS. 1 and 2;

FIG. 13 illustrates K-wires positioned in the bone fragments with those K-wires then received in the bone organizer or template shown in FIG. 5;

FIG. 14 is a sectional view of the bone organizer of FIG. 13 fixed with an adhesive cement for holding the bone fragments and K-wires in place while mending;

FIG. 15 illustrates K-wires positioned in bone fragments with those K-wires then received in a particularly preferred bone organizer or template and held in place in the organizer with a preferred fastener or grommet;

FIG. 16 is an enlarged view of a section of the bone organizer of FIG. 15 illustrating in detail a preferred fastener or grommet holding two K-wires;

FIG. 17 is a sectional view of a section of a bone organizer similar to that shown in FIG. 16 but with the K-wires anchored in place;

FIG. 18 is a plan view of the fastener or grommet;

FIG. 19 is a partial sectional view of the bone organizer with the K-wires in position from a first angle; and FIG. 20 is a partial sectional view of the bone organizer holding the K-wires in position from a second angle.

Referring to the drawing, FIGS. 1, 2, and 10-12 illustrate a preferred surgical hammer as described in my application Ser. No. 08/260,402 noted above, the disclosure of the application being incorporated herein by reference, which describes a device for driving K-wires into bone fragments and into the bone. Briefly, the device comprises an elongated housing member 10 having retained within that elongated housing member an elongated barrel member or hand piece 14 externally threaded at a first end 20, and internally threaded at its second end 21, and having an internal passageway 33 extending from its second end to its first end for passage of a K-wire or the like. An end-tip member 24 having internal threads, also having an internal passageway 32 extending therethrough, is screwed onto the first end 20 of the first elongated barrel member 14. The first barrel member and end-tip are constructed and arranged to house a collet 26 again having an internal passageway 27 for receiving a K-wire and holding the wire fast. The diameter of the passageway of the collet is designed to accommodate K-wires having diameters of from less than 1 up to about 5 mm. A second barrel member 30, preferably having an enlarged end 36 for turning and an internal passageway 31, is screwed into the first end 21 of the first barrel member 14. A slap hammer 34 is positioned on the second barrel member constructed and arranged to slidably ride on the second barrel member. The housing has detents at the internal surface of the housing spaced from each end for receiving a lock washer 18 positioned around the first barrel member. When the individual members of the device are in operable associate, a passageway for a K-wire or the like extends entirely through the device. The collet is chosen according to the selected diameter of the wire. The lock washer on the first barrel member engages the detents in the internal surface of the housing, locking the two together. Accordingly, when the second barrel member is rotated, all components of the device rotate within the housing. Since the collet firmly engages the K-wire, the K-wire also rotates. When the slap hammer is slapped against the second end of the housing, a K-wire within the passageway is driven forward and into an object such as a bone or a bone fragment or the like. The device provides, therefore, a relatively simple tool which permits the precision driving of a K-wire or the like into bone fragments for positioning and then holding the fragments in place while mending as shown in, for example, FIGS. 6, 7, 13 and 15.

Figure 6:
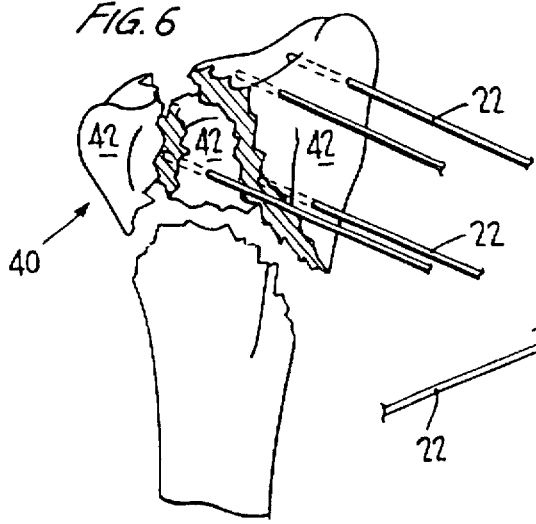
FIG. 6 illustrates a fragmented bone carrying a plurality of K-wires.
Figure 7:
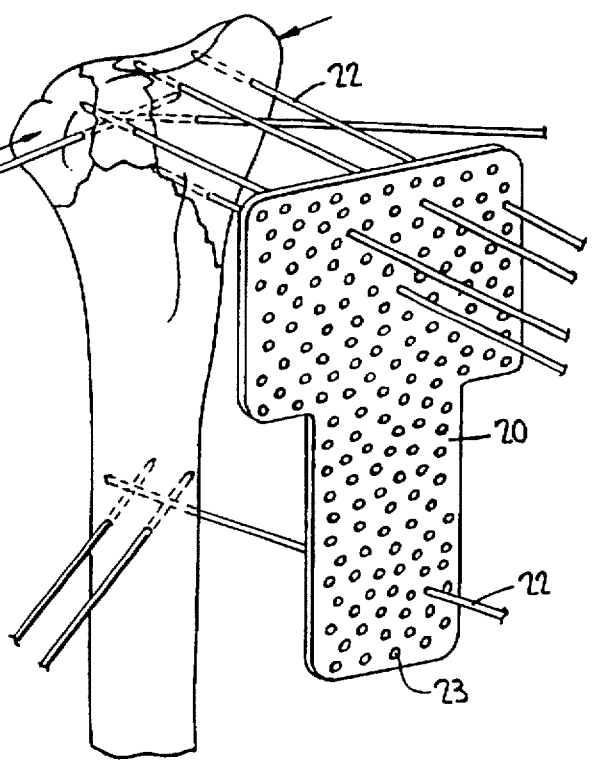
FIG. 7 illustrates the placement of the K-wires of FIG. 6 in the template shown in FIG. 3.

FIG. 3 illustrates a first template 30 or bone organizer in the shape of a "T" having a plurality of holes 24 in the template. FIG. 6 illustrates a fractured wrist bone 40 where the bone is in a number of pieces 42, receiving a plurality of wires 22 which are positioned with precision in the bone pieces using the surgical hammer shown in FIGS. 1 and 2. As shown in FIG. 7, the holes 23 in template 20 receive a plurality of K-wires. It is noted that the drawing, for simplification, does not show all the holes or show them in the same location. Because of the configuration of the template and the random distribution of the holes, the K-wires can be conveniently placed into the holes, even though the K-wires are on different planes.

Figure 8:
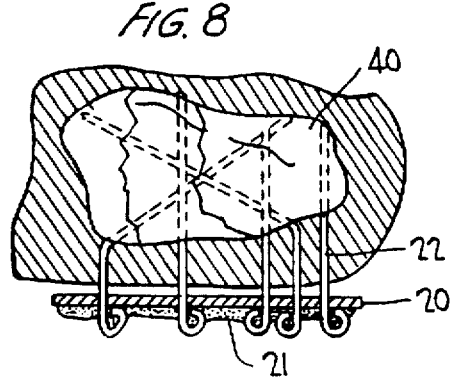
FIGS. 8 and 9 are sectional views of the template shown in FIG. 7 with the K-wires anchored to the template and cemented.
Figure 9:
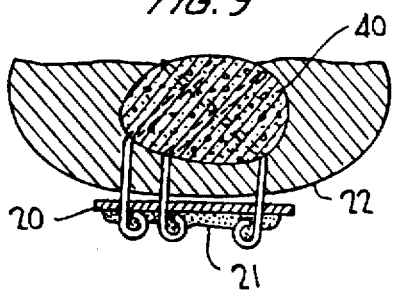

FIG. 8 illustrates the wrist fracture with the ends of the K-wires being bent over engaging the template and the wires then being cemented into position with a common adhesive, such as a polymer cement. A particularly suitable cement is a radiolucent methylmethacryate polymer. FIG. 9 is a cross-sectional view and illustrates the bone of the arm receiving K-wires 22 which have been driven into the bone as opposed to the bone fragments. The cement 21 will hold the template as well as the bone fragments precisely positioned while the bone fragments mend. When the mending is complete, the template and K-wires can be removed and, since the template is relatively inexpensive, it can be discarded.

FIG. 4 illustrates a square thin sheet of metal plate 50 having a plurality of holes 52 distributed therein. FIG. 5 illustrates the sheet of FIG. 4 fabricated into a bone organizer 51 having a series of corrugations 54 with the first end 56 of the sheet fan-shaped and the second end 58 of the sheet pressed together. It is noted again that the drawing, for simplification, does not show all the holes or show them in the same location. As shown in FIG. 13, the bone organizer 51 is ideally suited for receiving the K-wires, regardless of what plane the K-wires are on when positioned in the bone fragments. Because of the corrugations and fan-shaped configuration of the template, the template can be spread out or pressed together to accommodate bones of different sizes and any number of K-wires fitted into the different bone fragments in a plurality of planes.

FIG. 14 illustrates a sectional view of the arrangement shown in FIG. 13 after the K-wires have been cut off, bent over, and cemented to the bone organizer. Again as shown in FIGS. 6-9, after the bones have mended, the K-wires and template are removed and because of the inexpensive nature of the template, it can be discarded.

FIG. 15 illustrates a bone organizer 61 having a plurality of flat strips or bars 60 and 62 of a thin metal fastened together at one end with a corrugated rectangular sheet 64 and at the other end with a thin metal strip 66. Bars 60 are in a first plane and bar 62 in a second plane. Corrugated rectangular sheet 64 has alternate furrows 68 and ridges 70. A plurality of holes 63 for receiving K-wires 22 and a fastener 80 are on the ridges. Strip 66 shaped to receive and hold bars 60 and 62 also have holes 63 for receiving K-wires 22 and a fastener 80. As illustrated, the bone organizer can be arranged by flexing or bending of the corrugation to fit around a bone of varying sizes, such as a wrist bone, to receive the K-wires 22 from a plurality of planes.

As shown in FIGS. 16-18, fastener or grommet 80 comprises a body portion 82 having a threaded central hole 84 for receiving a screw member 85 and a plurality of recesses 86 leading into the central hole 84 and a hole 88 in each of the recesses adjacent to the central hole to receive K-wires. The received K-wires are bent over outwardly from the central hole to lie in the recesses. The head of the screw member will retain the K-wires in a fixed position.

The device of FIG. 15, as apparent, does not anchor the K-wires to the template with cement, but rather, uses a grommet or fastener. The grommet permit the anchoring of from anywhere from 2 to 4 K-wires. As shown in FIGS. 19 and 20, the first K-wires are inserted through the bars 60 or side members of the template and into the wrist bone at an angle ranging from 13° to 30°, preferably 20°. This is referred to as the radial angle. See FIG. 19. It is also necessary that there be a radial tilt of from 8 to 28°, preferably 110°. See FIG. 20. Once the first K-wires are inserted into the wrist bone, a second K-wire is inserted through the template towards the end of the bars 60 and away from the wrist bone as shown in FIG. 19. The template is, at the time the second K-wire is inserted, moved away from the arm by about 2 centimeters. When the second K-wire is inserted it will provide the correct distal length to permit proper mending of the fracture. Thereafter, additional wires can be inserted through the top and opposite side of the template for stability or the like. The device, therefore, provides for the correct radial angle, correct radial tilt and the correct radial length for maintaining of the fracture for mending. As a result of the locking member for the K-wires and the strength of the template, the device cannot move upward or downward or rotate but will remain stationary. A critical feature of the device is the ability to use as many K-wires as necessary but, moreover, provides for the ability to take a K-wire out and put in a new K-wire, i.e., there are 4 pin sites at one location.

The sequence is advantageous to the method. Thus, the operation preferably will be performed as follows:

1. Reduction of fracture using suitable technology.
2. Place a small incision at the base of the fracture.
3. Put the side member of the template on the skin and insert K-wires through the incision lined up with the long axis of the radius of the wrist at an approximate 20° angle. Lock the K-wires at the correct radial angle and radial tilt.
4. Insert a second K-wire rearward of the first K-wire into the arm bone away from the first K-wires. Adjust the radial length so that the fracture is held firm and cannot travel distally. Thereafter, insert the additional K-wires.

The device of FIG. 15 is designed for either a left or right wrist. It cannot be used interchangeably.

Accordingly, the present invention provides a simple method of maintaining reduction of a distal radius fracture of the wrist comprising inserting a plurality of K-wires into the bone fragments in a plurality of planes and after the K-wires are inserted, they are positioned in a bone organizer as shown in the drawing, which is designed to receive a plurality of K-wires through randomly distributed holes from a variety of planes. The K-wires are then anchored to the bone organizer and after being anchored are fixed in place as shown in the drawing. After the bone is mended, the K-wires and bone organizer are removed and discarded.

In summary, the present invention, and particularly the design of FIGS. 5 and 15, provides for:

1. Progressive stability against compression, bending and rotation. The corrugations in the template provide resistance against compression and bending. By compression of one end of the device into a fan-shape, rotational deformity is prevented and bending and compression is eliminated.
2. Accommodation of any size wrist by the accordion like nature of the bone organizer.
3. Adaptable to either the right or left wrist.
4. Light weight.
5. Radiolucency allowing radiologic visualization of the fracture by use of light weight aluminum.
6. Inexpensive in that the design is simple, permitting use of a cheap metal such as aluminum.
7. The device, because of its inexpensive nature, is disposable.
8. Malleability in that it can be adjusted to varying sizes to catch pins or K-wires.

The present invention provides, therefore, a simple inexpensive method for reducing a fracture, particularly a distal radius fracture of the wrist, without using expensive devices for the fixation.

It is noted that all metal preferably should be of such quality that it allows the X-ray to view the underlying bone (i.e., radiolucent) to allow proper positioning of the pins in the fracture fragments.

Although only a limited number of embodiments of the invention are disclosed herein, it is to be understood that various modifications can be made without departing from the spirit of the invention and the scope of the pending claims.

It is claimed:

1. Method of repairing a bone fracture comprising the steps of:
   a) arranging the bone pieces of the fractured bone and inserting a plurality of wires into said bone pieces;
   b) providing a template having a plurality of randomly distributed holes therein, said template having a first and second end, said first end being wider than said second end and having a greater number of holes therein relative to said second end;
   c) arranging the wires of step a in the holes of said template whereby a greater number of wires are in the first end thereof than in said second end;
   d) positioning the template adjacent to the bone fracture;
   e) anchoring the ends of said wires to said template; and
   f) fixing said ends of said wires to said template.
2. The method of claim 1 wherein said wires are inserted into the bone pieces on more than one plane.
3. The method of claim 2 wherein the wires are also inserted into the fractured bone away from the bone fracture and said wires are also arranged in said template, anchored and fixed.
4. The method of claim 1 wherein the template is a corrugated metal sheet having randomly distributed holes with one end of said sheet pressed tightly together thereby providing a fan-like shape with said wires being primarily positioned in the wide end of said template.
5. The method of claim 1 wherein the template comprises side bars and a central bar, said side bars being on a different plane from said central bar, said bars being held together in spaced relation at a first end by a rectangular metal sheet having alternate furrows and ridges and being held together in spaced relation at the second end by a thin metal strip, said ridges and side bars having a plurality of holes therein for receiving and retaining a fastener, said fastener having a body portion and a screw portion, said body portion having a central vertical opening for receiving said screw portion and a plurality of vertical openings adjacent to said central opening for receiving K-wires, said screw member being constructed and arranged to hold such K-wires in fixed position.
6. The method of claim 5, said body position includes recesses extending outwardly from said central opening to receive K-wires.

* * * * *